United States Patent [19]
Parodi et al.

[11] Patent Number: 5,489,664
[45] Date of Patent: Feb. 6, 1996

[54] MICROWAVE-POLYMERIZABLE ISOCYANATE/EPOXY RESINS FOR HEAVY-DUTY APPLICATIONS

[75] Inventors: Fabrizio Parodi, Genoa; Renata Gerbelli, Parma, both of Italy; Mark De Meuse, Robbinsville, N.J.

[73] Assignees: Enichem S.p.A.; Eniricerche S.p.A., both of Milan, Italy

[21] Appl. No.: 336,048

[22] Filed: Nov. 4, 1994

[30] Foreign Application Priority Data

Nov. 11, 1993 [IT] Italy ................... MI93A2401

[51] Int. Cl.$^6$ .................. C08G 18/00; C08G 18/58; C08G 18/18; C07C 255/13
[52] U.S. Cl. .................. 528/73; 525/528; 522/65; 522/78; 522/166; 522/170; 522/173; 524/847; 524/871
[58] Field of Search ................. 528/73; 525/528; 522/65, 78, 166, 170, 173; 524/847, 871

[56] References Cited

U.S. PATENT DOCUMENTS 4,033,911  7/1977  Sander et al. .
5,288,833  2/1994  Parodi et al. .
5,314,983  5/1994  De Meuse et al. .............. 528/73

FOREIGN PATENT DOCUMENTS 1384206  4/1965  France .

*Primary Examiner*—Frederick Krass
*Attorney, Agent, or Firm*—Oblon, Spivak, McClelland, Maier & Neustadt

[57] ABSTRACT

Crosslinkable liquid composition based on organic isocyanates and epoxy compounds, comprising the following components:
(A) an organic polyisocyanate;
(B) a polyepoxide or mixture of a polyepoxide and a monoepoxide; and
(C) a catalyst constituted by at least one cyanoderivative containing a quaternary nitrogen atom,
which composition can be polymerized at temperatures of 40° C. or higher, by a process comprising exposure thereof to a non-ionizing electromagnetic radiation having a frequency comprised in the microwave range of frequencies, to obtain a solid material endowed with an excellent combination of physical, chemical and mechanical properties.

30 Claims, No Drawings

MICROWAVE-POLYMERIZABLE ISOCYANATE/EPOXY RESINS FOR HEAVY-DUTY APPLICATIONS

DESCRIPTION

The present invention relates to isocyanate/epoxy compositions for heavy-duty applications, which compositions are polymerizable under microwave radiation.

In particular, the present invention relates to particular organic compositions comprising at least a compound carrying more than one isocyanate group (—NCO), and at least a compound carrying at least one epoxy group, which compositions are polymerizable to a crosslinked material having an excellent combination of chemical, physical and technological properties. The present invention relates further to a process for polymerizing said compositions by applying an electromagnetic radiation in the microwave range of frequencies.

Several industrial sectors call for high-performance crosslinkable resins (also called thermosetting resins) for fabrication of high-quality and long-endurance polymeric articles for heavy-duty applications. Such thermosetting resins must have a high fluidity before polymerization, as well as an excellent combination of chemical, physical and mechanical properties after being polymerized in the so-called curing and, eventually, post-curing cycles.

Particularly desirable are those resins which are rapidly polymerizable under appropriate conditions, but have also to remain liquid at room or, preferably, rather high temperatures long enough to meet the critical requirements of important discontinuous and continuous technologies where the thermosetting resin is necessarily fed as mono-component mixture, batchwise prepared and stored even several hours before use. Such a time interval, during which a thermosetting resin remains liquid and handable, is generally known as pot-life.

Examples of said technologies are:
a) resin casting, for fabrication of a variety of articles such as electrical insulators, connectors and relays, as well as to make insulating or protective coatings of electrical motors or other electrical machinery;
b) embedding and encapsulation, by vacuum, pressure or combined vacuum/pressure casting, of electrical/electronic devices, such as transformers, capacitors, etc.;
c) resin pultrusion and pulforming with reinforcing fibers, for manufacturing of structural beams, bars, etc., for industrial and civil constructions and transportation, particularly where elevated peak and/or service temperatures are involved.

These technologies require resins with appropriately low viscosities. Generally, a resin having a low viscosity is particularly suitable for use in most of preparation, handling and processing stages thereof, such as, for instance, the mixing of the various components to an homogeneous mixture; the accurate vacuum-degassing of the compositions (especially when considerable amounts of solid fillers are involved); the resin metering, pumping, suction or casting from tanks into the appropriate molds or cavities through pipes or channels; or, further, the fiber impregnation in pultrusion and pulforming.

The low viscosity required for a resin to be used in a given technology, is often achieved by warming up the same, provided that it does not cause early polymerization during the above preparation, storage and handling steps, implying a time interval eventually prolonged to several hours before the resin molding is to be accomplished.

However, a fast hardening is obviously highly desirable during the curing step, in order to shorten the residence times in molds or ovens, thus increasing the hourly production of articles.

Tipically, a heavy-duty thermosetting resin is characterized by a high softening point (>200° C.), low flammability, good hydrolytic, chemical and solvent resistance, high dielectric strength, high modulus and dimensional stability. High performance resins already available are, e.g., epoxy resins cured with anhydrides or aromatic polyamines, polyimides and other heterocyclic resins, bismaleimides, etc.

Although satisfactory for several appliances, these resins are affected by important drawbacks, like, for instance:

(i) in general, slow hardening cycles, unsuitable for fast tranformation technologies unless high curing temperatures are adopted, which, in turn, may cause overheating due to the polymerization exotherm, with consequent thermodegradation of the polymeric material;

(ii) high viscosities and slow motion in the pipes for resin feed-up (epoxy resins, e.g., have viscosities in the range of thousands and of hundreds of centipoise at room temperature, and at 50° C., respectively).

Suitable thermosetting systems for fast polymerization at lower temperatures have been developed, such as, e.g., the epoxy resin compositions with aliphatic or cycloaliphatic polyamine hardeners, or the epoxy resins containing boron trifluoride complexes as catalysts. On the other hand, such compositions are characterized by a pot-life unsuitably short for preserving the product long enough according to the requirements of several industrial processes.

It is known that polymeric products containing isocyanurate (I) and/or 2-oxazolidone (II) moieties are attainable by polymerization of compositions based on polyisocyanates and epoxy compounds.

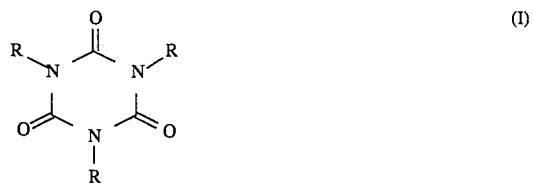

These thermosetting materials are characterized by softening temperatures normally higher than 250° C., an excellent chemical, solvent and hydrolytic resistance, low flammability (which can be further improved up to self-estinguishment by adding mineral fillers), and satisfactory dielectric properties. Particularly, such materials can be obtained by polymerizing reactive compositions containing polyisocyanate and epoxy resins, which compositions have viscosities of a few hundreds centipoise at room temperature and of tens centipoise at 50° C.

It is known, as well, that the polymerization of compositions containing di- or poly-isocyanates and mono- or poly-epoxides can be promoted by different catalysts, e.g. tertiary amines, alkylimidazoles, quaternary ammonium salts, tetraalkyl-phosphonium halides, or complexes of a boron trihalide with a tertiary amine, according to U.S. Pat. Nos. 4,131,600, 4,562,227, 4,564,651, 4,576,768, 4,631, 306, or, also, to German Patents 3,323,153, 3,644,382 and 3,807,660 among others.

Normally, the isocyanate/epoxy thermosetting compositions according to the prior art are characterized by satisfactory pot-life values varying from days up to months at the usual storing temperature, and comprised as well in the range of some hours at temperatures comprised within the range of from 40° to 60° C. A pot-life of hours is critical when the thermosetting composition is maintained in a container at such temperatures before use in the common molding technologies. However, the polymerization and hardening of such compositions requires to be typically accomplished by heating them for 1 to 8 hours at temperatures comprised within the range of from 80° to 160° C., and, preferably, comprised within the range of from 100° to 140° C. Moreover, the polymerization need to be completed by submitting the compositions to a subsequent thermal treatment of post-curing at temperatures higher than 150° C., usually within the range of from 180° to 220° C., for several hours, in order to attain a high softening temperature (normally corresponding to the glass transition temperature $T_g$ in amorphous and homogeneous materials).

Such long polymerization and working times are clearly a severe obstacle to a wider use of epoxy/isocyanate compositions. On the other hand, high polymerization rates with the above-mentioned catalysts are only possible by starting from considerably high temperatures. This implies a strong heat evolution due to the highly exothermic polymerization reaction, possibly with production of overheating in several zones of the reacting mass, especially when very thick, and consequent decomposition, bubbling, sometimes up to foaming, and embrittlement of the resulting polymeric material.

The problems of overheating, with a fast polymerization rate, can be solved as reported, e.g., in the U.S. Pat. No. 5,145,880 and in the European Patent Publication 514,994, wherein thermosetting compositions are described which are based on mixtures of polyisocyanate and epoxy compounds containing catalysts bearing quaternary 13-hydroxyalkylammonium halide groupings; as well as in the European Patent, Publication No. 546,602, regarding the liquid isocyanate-epoxy compositions catalyzed by solutions of alkaly metal halide in polyoxyalkylenic compounds. Such compositions are capable of hardening in times of the order of 5–30 minutes at relatively low temperatures, comprised from 30° to 60° C.

However, they do allow extremely short preparation and working times at temperatures comprised within the range of from room temperature to 60° C., which are unsuitable for industrial applications requiting a prolonged pot-life as previously said.

It is also known that some substances, having a high dielectric loss factor, can be easily heated by submitting them to an electromagnetic field in the microwave range of frequencies.

Microwave treatments have been proposed, indeed, for accelerating the cure of particularly suitable crosslinkable resins, like those containinig a highly dipolar group such as sulfonyl or ester. Applications of such microwave technologies are described, for example, in the publication of J. Wei et al., in Proc. 5th Amer. Soc. Comp., 1990, page 239, wherein epoxy resin systems are described which are cured with 4,4'-diaminodiphenylsulfone (DDS) under microwave irradiation. In this case, however, the sulfonyl group implies a very slow polymerization rate as well, whereas, with other epoxy systems containing less polar groupings than sulphonyl, the susceptibility to microwave action is much lowered and can hardly be applied to industrial uses.

In spite of some good results obtained by the application of microwave technology in other fields, this does not seem however to have been sufficiently developed in the field of isocyanate/epoxy compositions, with the exception of the process indicated in U.S. patent application Ser. No. 07/973, 743 now U.S. Pat. No. 5,314,983, filed by the Applicant, which describes a method for the rapid microwave polymerization of compositions containing polyisocyanates, epoxy compounds and the known polymerization catalysts for these systems. Although this latter procedure represents a considerable step forward in the technology with respect to the known art, it does not however adequately solve the problem of a short hardening cycle associated with a prolonged pot-life of the thermosetting systems mentioned above.

A need is therefore felt, in the technological field of high-performance thermosetting resins, for compositions and polymerization methods which generally overcome the above drawbacks without jeopardizing in any way the technological advantages obtained with the systems presently in use.

One of the purposes of the present invention is therefore to obtain a crosslinkable composition having a pot-life, at room or moderately higher temperature, which is long enough to allow its processing with a wide range of technologies, and at the same time, capable of being rapidly polymerized both by thermal heating and, at lower temperatures, by exposure to non-ionizing electromagnetic radiation in the field of microwave frequencies, and also a combination of the two technologies.

A further purpose of the present invention is to provide a process for a rapid and manageable polymerization of said composition, without or with very slight overheating, to obtain a crosslinked polymeric material with a high softening point, said procedure being preferably used for the rapid manufacture of high quality articles or devices for heavy-duty applications from the thermal, mechanical or electrical aspect.

The Applicant has now found that these and other objectives which emerge in the description, can be easily and surprisingly reached by crosslinkable liquid compositions containing at least one compound having more than one isocyanate group (—NCO), at least one compound having at least one epoxy group and at least one particular catalyst soluble in the liquid mixture, said compositions having a prolonged latent period at temperatures up to 70° C., and yet capable of being rapidly polymerized, also at low temperatures, by microwave radiation.

The present invention therefore relates to a crosslinkable liquid composition based on organic isocyanates and epoxy compounds, polymerizable, already at temperatures of 40° C. or higher, by exposure to a non-ionizing electromagnetic radiation having a frequency comprised in the microwave range of frequencies, to obtain a solid material, said composition comprising:

(A) at least one organic polyisocyanate;

(B) at least one polyepoxide or mixture of a polyepoxide and a monoepoxide; and (C) from 0.05 to 5 parts by weight per 100 parts of (A) plus 03), of at least one cyanoderivative containing a quaternary nitrogen atom, having the following general formula (III):

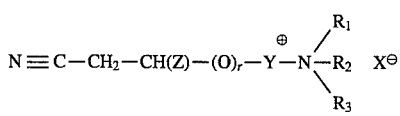

wherein:

Z can be hydrogen or an aliphatic radical having 1 to 10 carbon atoms or cyclo-aliphatic or heterocyclic having 3 to 10 carbon atoms or aromatic containing 6 to 10 carbon atoms and, preferably, Z is hydrogen, methyl, ethyl, n-propyl, cyclohexyl or phenyl;

Y is a non-monovalent organic radical of an aliphatic nature having 2 to 16 carbon atoms, or of a cyclo-aliphatic or heterocyclic nature having 5 to 16 carbon atoms, or of an aromatic nature containing 6 to 16 carbon atoms;

$R_1$ and $R_2$, the same or different, can be independently aliphatic, cyclo-aliphatic, aromatic or heterocyclic radicals, or $R_1$ and $P_1$ can be linked to each other to form part of a heterocyclic, aliphatic or aromatic structure, with at least 5, preferably 5 to 8, atoms in the cycle, comprising the quaternary nitrogen atom, and $R_1$ and $R_2$ have a total of 2 to 20 carbon atoms, or Y and $R_1$, or Y, $R_1$ and $R_2$ are linked to each other to form a heterocyclic, mono or bicyclic, aliphatic or aromatic structure respectively, having at least 5 atoms, preferably 5 to 8 atoms in each cycle, comprising the quaternary nitrogen atom;

$R_3$ is an aliphatic radical, preferably alkyl, containing 1 to 20 carbon atoms, or an aryl-alkyl radical having 7 to 20 carbon atoms; r can be 0 or, preferably, 1; and $X^-$ is a halide anion selected from chloride, bromide or iodide.

For the purposes of the present invention, $X^-$ is preferably iodide or bromide.

The present invention also relates to the group of compounds (C) represented by the previous formula (III).

A further object of the present invention is a process for the polymerization of the above crosslinkable liquid compositions via microwaves, comprising the following steps:

(i) mixing components (A), (B) and (C) until a homogeneous mixture is obtained;

(ii) charging the mixture prepared in (i) into an apparatus for treatment with electromagnetic radiation with frequencies within the range of 0.5 GHz to 20 GHz (microwaves);

(iii) subjecting the mixture charged into the apparatus of point (ii), to microwave radiation for a period of more than 0.5 minutes at a temperature not lower than 40° C., preferably between 40° and 80° C.

The term crosslinkable liquid composition, as used in the present invention and claims, indicates that the crosslinkable compositions of the present invention must be liquid at the mixing and processing temperatures and not necessarily at room temperature, although liquid compositions at room temperature are preferred.

In the crosslinkable liquid compositions of the present invention component (C) having formula (III), which is also object of the present invention, has the function of polymerization catalyst and will hereafter be referred to with this term in the present description.

Specific examples of $R_1$ and $R_2$ in formula (III) of component (C), although not limiting the capacity of the present invention, can be aliphatic groups such as methyl, ethyl, n-proyl, n-butyl, isobutyl, n-pentyl, n-hexyl, 2-methylhexyl, 2-ethylhexyl, n-octyl, n-decyl, n-undecyl, n-tetradecyl, n-octadecyl, 2-methoxyethyl, 2-ethoxyethyl, and the like; or aromatic groups such as phenyl, 4-methylphenyl, 3-methylphenyl, 4-ethylphenyl, 4-octylphenyl, etc. $R_1$ and $R_2$ preferred for the purposes of the present invention are those consisting of aliphatic groups.

In another embodiment of the present invention, in formula (III) the $R_1$ and $R_2$ groups are linked to each other to form a cyclic structure preferably having from 5 to 8 atoms in the cycle, which comprises the quaternary nitrogen atom and can also comprise other heteroatoms such as, for example, O, S and Si. Typical but not limiting examples of such structures are:

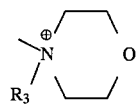

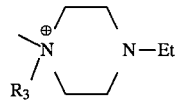

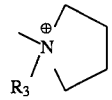

wherein $R_3$ has the same meaning defined above.

In accordance with one of the aspects of the present invention, Y in formula (III) is a divalent aliphatic organic radical having from 2 to 10 carbon atoms, or a divalent cyclo-aliphatic radical having from 5 to 10 carbon atoms, which can contain only carbon and hydrogen, or, in addition, one or more ether groups —O— and/or thioether groups —S—, far from each other and from the N and O atoms having formula (III) by at least two carbon atoms. Non-limiting examples of Y groups of an aliphatic or cyclo-aliphatic nature are: 1,2-ethylene, 1,3-propylene, 1,2-propylene, 1,4-tetramethylene, 1,6-hexamethylene, 1,4-cyclohexylene, (1,4-cyclohexane) dimethylene, oxydiethylene, dioxytriethylene, etc.

In accordance with another aspect of the present invention, the group Y in formula (II) is an aromatic or aliphatic-aromatic divalent radical, possibly also containing heteroatoms, preferably oxygen or sulphur, non-limiting examples of which are: 1,4-phenylene, 1,3-phenylene, 3,5-tolylene, α,α'-xylilenes, 1,4-naththylene, 1,5-naphthylene or 2,5-furylene.

According to a further aspect of the present invention the organic radical Y in formula (III) can also be linked to one or both of substituents $R_1$ and $R_2$ of the quaternary nitrogen atom to form part of a heterocyclic, mono- or bi-cycle structure, comprising the same quaternary nitrogen atom, the structure possibly containing one or more additional heteroatoms in the ring. Non-limiting examples of these heterocyclic structures within the range of the present invention are:

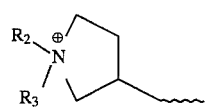

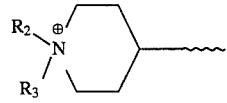

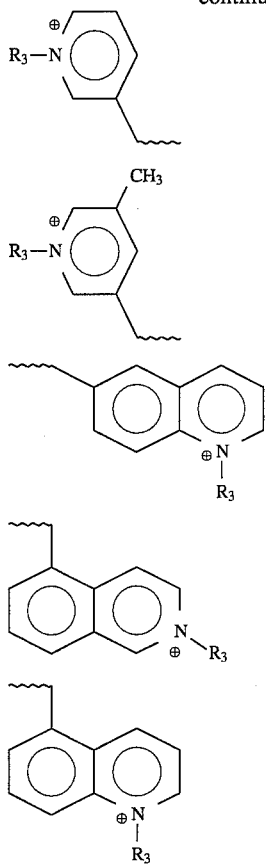

wherein $R_2$ and $R_3$ have the same meaning as described above.

Non-limiting specific examples of the group $R_3$ of formula (III) are methyl, ethyl, n-propyl, n-butyl, n-pentyl, 3-methylbutyl, n-hexyl, n-octyl, n-decyl, n-undecyl, n-dodecyl, n-hexadecyl, n-octadecyl, allyl, crotyl groups etc., or benzyl alkyl-aryl, α-xylyl groups, etc.

According to a particularly preferred aspect of the present invention, at least one of the groups $R_1$, $R_2$ or $R_3$ is an aliphatic or arylaliphatic group having 6 to 20 aliphatic carbon atoms.

The catalyst (C) of the present invention can be either liquid or solid at room temperature. According to a preferred aspect of the present invention, the catalyst (C) is liquid at a temperature of 60° C. at atmospheric pressure or, in a particularly preferred form, at a temperature of 30° C.

However catalysts having formula (III) are preferred which are soluble in the mixtures of (A)+(B). Particularly preferred are those soluble in one of the components (A) or (B) of the present compositions or, even better, separately in both.

Illustrative but non-limiting examples of catalysts having formula (III) of the present invention are:

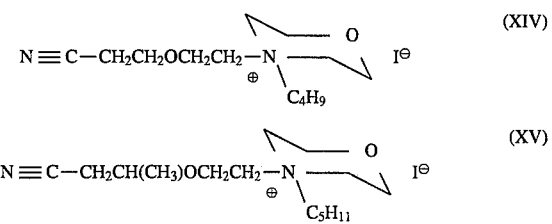

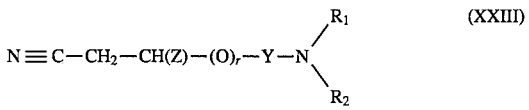

The catalyst (C) of the present invention can be obtained with a synthetic method wherein, in a first step, a tertiary cyanoalkylamine is prepared having the following formula (XXIII):

wherein Z, Y, $R_1$, $R_2$ and "r" have the same meaning previously described for the products having formula (III);

and, in a second step, the alkylation of this cyanoalkylamine is carried out, by the reaction of an aliphatic or arylalkyl halide $R_3X$, wherein $R_3$ has the same meaning previously indicated for the corresponding symbol of formula (III) and X is a chlorine, bromine or iodine atom, to form the product having formula (III) containing a quaternary nitrogen atom.

The tertiary cyanoalkylamines in formula (XXIII), or their mixtures, can be prepared with one of the normal synthetic methods of organic chemistry suitable for the purpose. In the preferred case wherein "r" in formula (XXIII) is equal to 1, these products are conveniently prepared using a known cyanoalkylation method in which a tertiary aminic compound containing a hydroxylic group, having the following formula (XXIV):

$$HO-Y-NR_1R_2 \qquad (XXIV)$$

wherein Y, $R_1$ and $R_2$ have the same meaning as the corresponding symbols in formula (III) above, or a mixture of these compounds, is reacted with an α,β-unsaturated nitrile, or with a mixture of, α,β-unsaturated nitriles having the following formula (XXV):

$$N{\equiv}C\text{—}CH{=}CH(Z) \qquad (XXV)$$

wherein Z has been previously defined in formula (III).

According to the synthesis method specified above, the hydroxyaminic compound having formula (XXIV) is preferably selected from the following groups of compounds: aminoalcohols and aminophenols having a tertiary aminic group, comprising those containing ether groups in the molecule, hydroxypyridine, hydroxyquinolines, hydroxyisoquinolines. Examples of these compounds which can be advantageously used comprise: 2-dimethylaminoethanol, 2-diethylaminoethanol, 2-dibutylaminoethanol, 3-dimethylamino-1-propanol, 3-dimethylamino-2-propanol, 3-diethylamino-1-propanol, N-(2-hydroxyethyl)pyrrolidine, 1-ethyl-3-hydroxypyrrolidine, N-(2-hydroxyethyl)piperidine, 1-ethyl-3-hydroxypiperidine, N-(2-hydroxyethyl)morpholine, 2-(ethylphenylamino)ethanol, 2[ethyl(3-methylphenyl)amino]ethanol, 4-dimethylaminophenol, 3-diethylaminophenol, 3-hydroxypyridine, 4-hydroxypyridine, 3-hydroxy-5-methylpyridine, 6-hydroxyquinoline, 5-hydroxyquinoline, 5-hydroxyisoquinoline.

The $\alpha,\beta$-unsaturated nitrile having formula (XXV) is preferably selected from acrylonitrile, crotononitrile, 2-pentenenitrile, 2-hexenenitrile, 3-cyclohexylacrylonitrile and cinnamonitrile.

According to the above method for the preparation of cyanoalkylamine having formula (XXIII), the hydroxyaminic compound (XXIV) and $\alpha,\beta$-unsaturated nitrile (XXV) are reacted in such quantities that the molar ratio between the hydroxylic groups of the compound (XXIV) and the olefinic double bond of the nitrile (XXV) is not lower than 1 and, is preferably equal to 1. The reaction can be carried out using the conventional experimental procedures in organic chemistry for the cyanoethylation and, in general, cyanoalkylation reactions.

In particular, the reaction between the tertiary hydroxyaminic compound (XXIV) and the $\alpha,\beta$-unsaturated nitrile (XXV) is conveniently carried out in the presence of a suitable catalyst consisting of a strong base preferably selected from: hydroxides of tetraalkyl-ammonium and phosphonium, such as tetramethylammonium hydroxide, trimethylbenzylammonium hydroxide, tetrabutylphosphonium hydroxide and strong anion-exchanger resins; hydroxides of alkali metals such as lithium, sodium and potassium hydroxides; alkoxides of alkali metals such as potassium methoxide and sodium ethoxide; hydrides of alkali metals such as lithium and sodium hydrides; amides of alkali metals such as sodium- and potassium- amide and lithiumdiethylamide, and mixtures of these.

As specified above, the tertiary cyanoalkylamine having formula (XXIII) is reacted, in a second step, with a halide $R_3X$, to obtain the cyanoderivative having formula (III) containing a quaternary nitrogen atom which forms the polymerization catalyst (C) of the compositions of the present invention. The molar ratio between the halide and tertiary aminic groups of the cyanoalkylamine must in this case be equal to or greater than 1 and preferably between 1.0 and 1.1. The reaction can be conveniently carried out using the methods generally known in organic chemistry for the quaternization of the tertiary amines.

$R_3X$ halides which can be used in a particularly advantageous way in the present invention are alkyl monoiodides and monobromides or their mixtures.

Preferred alkyl monoiodides comprise iodomethane, iodoethane, 1-iodopropane, 1-iodobutane, 1-iodopentane, 1-iodo-3-methylbutane, 1-iodohexane, 1-iodoheptane, 1-iodo-octane, 1-iododecane, 1-iodododecane, 1-iodohexadecane, 1-iodo-octadecane, allyliodide, benzyliodide, and their mixtures.

Suitable alkyl monobromides comprise bromomethane, bromoethane, 1-bromopropane, 1-bromobutane, 1-bromopentane, 1-bromo-3-methylbutane, 1-bromohexane, 1-bromoheptane, 1-bromo-octane, 1-bromodecane, 1-bromododecane, 1-bromohexadecane, 1-bromo-octadecane, allylbromide, crotylbromide, benzylbromide, and their mixtures.

The above cyanoalkylation and quaternization reactions for the preparation of the catalyst (C) of the present invention can be carried out using only the reagents and catalysts mentioned above, or in the presence of suitable solvents which are inert or not very reactive towards the functional groups present in the reaction mixtures and, preferably, are volatile enough to allow them to be easily removed by distillation. Solvents which can be used for this purpose comprise tetrahydrofuran, dioxane, 1,2-dimethoxyethane, diisopropylether, terbutylmethyl-ether, hexane, heptane, cyclohexane, methylcyclohexane, benzene, toluene, nitromethane, and their mixtures.

The preparation of catalyst (C) is preferably carried out without solvents or in the presence of the smallest possible quantity of these.

For purely illustrative purposes which do not limit the scope of the present invention, a typical and convenient procedure for the preparation of the catalyst (C) comprises the following steps:

I-a) the $\alpha,\beta$-unsaturated nitrile (or a mixture of different, $\alpha,\beta$-unsaturated nitriles) is slowly added, under stirring, to a liquid mixture consisting of the tertiary hydroxyaminic compound of formula (XXIV) (or a mixture of these tertiary hydroxyaminic compounds), the catalyst consisting of one of the strong bases mentioned previously, and possible solvent or mixture of solvents, maintained at a temperature within the range of 0° to 80° C.; said strong base being present in a quantity of 0.5 to 5 milliequivalents with respect to 100 g of the total mixture, comprising the $\alpha,\beta$-unsaturated nitrile;

I-b) the reaction mixture obtained in (I-a) is kept under stirring for a period of between 0.5 and 6 hours at temperatures of between 0° and 80° C.;

II-a) the alkyl monohalide is added to the mixture obtained in step (I-b), kept under stirring at a temperature of between 0° and 40° C., and the stirring is continued for a further period of 0.5 to 6 hours with the same temperature range;

II-b) the mixture obtained in step (II-a) is heated, under stirring, to a temperature of between 50° and 120° C. and kept at this temperature for a period of between 6 and 60 hours;

II-c) the possible solvent is removed from the mixture by evaporation at atmospheric pressure, or even better, at reduced pressure, to obtain a residue consisting of the polymerization catalyst (C).

Suitable organic polyisocyanates for use as component (A) in the compositions of the present invention are the organic compounds the average molecule of which contains more than one isocyanate group (—NCO). In particular, the organic polyisocyanates of the present invention are compounds having the following general formula (XXVI):

$$Q(NCO)_m \qquad (XXVI)$$

wherein "m" is a decimal higher than 1, and preferably is comprised within the range from 2 to 4; and Q is an organic m-valent radical of from 4 to 24 carbon atoms, of aliphatic, cycloaliphatic, aromatic, heterocyclic type, or of mixed type deriving from a combination of the previous ones.

A large number of isocyanates is known, having structures comprised in Formula (XXVI) above. Several of them have been reported, e.g., by A. A. R. Sayigh, H. Ulrich and W. J. Farissey, Jr., in "Condensation Monomers", edited by J. K. Stille and T. W. Campbell, published by Wiley-Interscience, New York, 1972, pages 369–476, the content thereof is herewith included as reference.

Also included in the scope of the present invention are polyisocyanates of formula (XXVI) the organic radical Q thereof contains heteroatoms not belonging to cyclic structures, as well as one or more functional groups different from isocyanate such as ether, thioether, ester, carbonyl, sulfonyl, amide, carbodiimide, urethonimine, urethane, allophanate, biuret groups, olefinic double bonds, acetylenic triple bonds, and still others known to the expert of the art.

According to a preferred form of practical embodiment of the present invention, polyisocyanates which are liquid at temperatures lower than 60° C., can be advantageously used as component (A).

Also, mixtures of different polyisocyanates of formula (XXVI), and preferably lo those mixtures which are liquid at temperatures lower than 60° C., can be used.

Aromatic polyisocyanates or mixtures thereof are preferably used as component (A) in the compositions of the present invention. Said aromatic polyisocyanates are characterized by the fact that the —NCO groups are directly bonded to an aromatic or heteroaromatic ring, and constitute the most of commercially available polyisocyanates.

Examples of aromatic polyisocyanates or mixtures thereof which can be used in the present invention comprise: toluene-2,4-diisocyanate , toluene-2,6-diisocyanate and their mixtures, diphenylmethane-4,4'-diisocyanate, diphenylmethane-2,4'-diisocyanate and diphenylmethane-2,2'-diisocyanate and their mixtures, naphthalene-1,5-diisocyanate, 1,4-phenylene-diisocyanate, 3,3'-dimethyldiphenylene-4,4'-diisocyanate, diphenylether-4,4'-diisocyanate and triphenylmethane-4,4',4"-triisocyanate. Other aromatic polyisocyanates which can be advantageously used are those polyphenylmethylene-polyisocyanates which can be obtained by phosgenation of the condensation products of aniline with formaldehyde.

Modified aromatic polyisocyanates, which can also be used as component (A) in the compositions of the present invention, are, e.g., the isocyanate adducts which can be obtained from the reaction of one mole of a polyol containing a number "p", equal to or higher than 2, of alcoholic hydroxy groups (—OH), with "p" moles of an aromatic polyisocyanate of the above cited type, and, in particular and preferably, with "p" moles of an aromatic polyisocyanate, preferably a diisocyanate, of the above cited type or a mixture thereof. Useable polyols to this aim are, e.g., ethylene glycol, diethylene glycol, triethylene glycol, tetraethylene glycol, propylene glycol, dipropylene glycol, tripropylene glycol, 1,3-butanediol and 1,4-butanediol, 1,5-pentanediol, 1,6-hexanediol, trimethyl-1,6-hexanediols, glycerol, 1,1,1 -trimethylolpropane, 1,1,1 -trimethylolethane, and mixtures thereof. Those isocyanate adducts are preferred which, as such or in admixture with one another or with other aromatic polyisocyanates, are liquid at temperatures lower than 60° C. Examples of isocyanate adducts, which are liquid at room temperature, though derived from an aromatic polyisocyanate which is solid at room temperature, are those adducts which can be obtained from the reaction of two moles of diphenylmethane-4,4'-diisocyanate with one mole of dipropylene glycol or triethylene glycol.

Other modified aromatic polyisocyanates which can be advantageously used, are the isocyanic prepolymers which can be obtained from the reaction of aromatic polyisocyanates selected from among those as defined hereinabove, as such or in admixture with each other, with one or more polymeric diol or polyol having an average molecular weight comprised within the range of from 200 to 15,000. Such isocyanic prepolymers can be obtained by reacting such amounts of polyisocyanates and of said diols or polyols, such that the molar ratio of isocyanate groups to hydroxy groups is equal to 2, or higher. Examples of polymeric diols or polyols, which are suitable for the preparation of said isocianic prepolymers, are polyoxyalkylenediols, such as poly(ethylene glycol), poly(propylene glycol), poly(tetramethylene glycol), poly(hexamethylene glycol) and the corresponding copolyoxyalkylenediols. Still other suitable polymeric polyols are those compounds which can be obtained by mono- or poly-oxyalkylenation of different, non- polymeric polyols, with alkylene oxides, such as ethylene oxide, propylene oxide, tetrahydrofuran, isobutylene oxide or mixtures thereof. Specific examples of said polymeric polyols are polypropoxylated 1,1,1 -trimethylolpropane, monopropoxylated or polypropoxylated glycerol, polypropoxylated sorbitol and polypropoxylated pentaerythritol.

Still other polymeric diols or polyols which can be used for the present invention are the polyesters containing 2 or more alcoholic hydroxy groups at their chain ends, and having an average molecular weight preferably comprised within the range of from 400 to 10,000. Examples of such polyester-polyols are those compounds which can be obtained by polycondensation of polycarboxylic, preferably dicarboxylic, acids, as such or in admixture with one another, with a polyol, or a mixture of several polyols, and preferably diols, of the above mentioned type, in such amounts as the molar ratio of hydroxy groups to carboxylic groups to be higher than 1. Suitable polycarboxylic acids for preparing said polyester-polyols are, e.g., phtalic acids, naphtalen di- or tri-carboxylic acids, trimellitic acid, adipic acid, glutaric acid, succinic acid and cyclohexanedimethyldicarboxylic acid.

Suitable polyester-polyols are also those which can be analogously obtained by polycondensation of said polyols and hydroxycarboxylic acids, or of polyols and mixtures of hydroxy carboxylic acids and polycarboxylic acids, especially mixtures of monohydroxy-monocarboxylic acids and dicarboxylic acids. Further included in the scope of the present invention are, as well, polyester-polyols, and preferably polyester-diols and polyester-triols, which can be obtained by polymerization of lactones, such as ε-butyrolactone, ε-caprolactone or still others, or mixtures thereof, which polymerization is initiated by means of a suitable amount of a non-polymeric polyol, and preferably a diol or a triol.

Still further polymeric polyols suitable for preparing isocyanic prepolymers for the present invention comprise other polymers containing at least 2 alcoholic hydroxy groups, such as, for example, polymers obtained by ozonolysis of oligomers or polymers of butadiene or isoprene or copolymers thereof, followed by reduction, as well as polymers attainable by copolymerization of vinyl compounds, such as acrylonitrile, vinyl chloride, styrene and still others, either as single compounds or mixed with one another, with at least one vinyl compound containing an alcoholic hydroxy group, such as hydroxyalkyl-acrylates or methacrylates, hydroxyalkyl-styrene, and still others.

According to the present invention, preferably used aromatic polyisocyanates (A) are those ones easily prepared or available from the market, and are liquid at temperatures not higher than 60° C., preferably not higher than 40° C. Preferred isocyanates of such type are, e.g., toluene-2,4-diisocyanate and toluene-2,6-diisocyanate and mixtures of such isomers, and, among these latter, in particular, the mixture wherein the ratio between the two 2,4- and 2,6-isomers is 80/20, which is currently available from the market. Other preferred polyisocyanates are diphenylmethane-4,4'-diisocyanate (or MDI), and the mixtures thereof with the corresponding isomers diphenylmethane-2,4'-diisocyanate and diphenylmethane-2,2'-diisocyanate, and, generally polyisocyanates of the above type which can be obtained by means of the phosgenation of the aromatic polyamines derived from the condensation of aniline with formaldehyde in various ratios to each other.

These latter polyisocyanates are commonly easily available commercial products designated "crude or polymeric MDI" by the experts of the art. They are constituted by more or less complex mixtures prevailingly comprising diphenylmethane-4,4'-diisocyanate and diphenylmethane-2,4'-diisocyanate together with other isomers thereof, and various polyphenylmethylene-polyisocyanates in variable mutual ratios. Such types of mixtures can additionally be comprised of isocyanates containing carbodiimide groups —N=C=N—, deriving from condensations between two isocyanate groups, as well as isocyanic adducts (or urethonimine groups) of said carbodiimidic compounds with said isocyanates.

Other polyisocyanates which can be advantageously used are the mixtures containing diphenylmethane-2,4'-diisocyanate and diphenylmethane-4,4'-diisocyanate in various proportions with each other, which can be obtained by means of the distillation of the above cited polymeric MDI, as well as the same residues from the same distillation, which are particularly rich in polyphenylmethylene-polyisocyanates.

Finally, the residues of distillation can be used as well, according to the present invention, which are constituted by complex mixtures of isocyanate group-containing compounds, which can be recovered from the preparation of commercial aromatic polyisocyanates, and, in general, from polyisocyanates different from the ones belonging to the family indicated hereinabove of the diphenylmethane based polyisocyanates, such as, e.g., the residues from distillation of toluene-diisocyanate.

The organic polyepoxides and monoepoxides suitable as the component "B" for the preparation of the compositions of the present invention are organic compounds with aliphatic, cycloaliphatic, aromatic, heterocyclic structure, or compounds with mixed structure deriving from a combination of the previous ones, whose molecule contain one (for monoepoxides) or more epoxy groups.

Such epoxy groups are known to be characterized by an oxyrane skeleton:

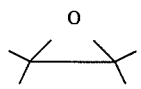

which may be primary or secondary as far as it is placed at one end or in the middle of the molecular chain.
Primary epoxy groups are preferred.

According to the present invention, the component (B) comprises also mixtures of polyepoxydes, or of polyepoxydes with monoepoxydes. The average number of epoxy groups per molecule of component (B) is a decimal number higher than 1, and preferably comprised between 1.8 and 4.0, extremes included. For the aims of the present invention, preferred polyepoxides, or mixtures thereof, contain an average of from 2 to 4 epoxy groups per molecule.

Any polyepoxide and monoepoxide which is known in the art, can be used according to the object of the present invention. A large number of diepoxides and polyepoxides of said type are listed, e.g., in the following references, together with several methods for the preparation thereof:

"Handbook of Epoxy Resins" by H. Lee and K Neville, McGraw-Hill, New York, (1967), pages 4–36 to 4–70, and "Epoxy Resins. New Results and Developments", by F. Lohse, Die Makromolekulare Chemie, Macromolecular Symposia, vol. 7, pages 1–16 (1987), the content of which is herewith enclosed as reference.

The diepoxides and polyepoxides which can be used comprise the polyglycidylethers of bisphenols and polyhydric phenols, such as 2,2-bis(4-hydroxyphenyl)propane ("bisphenol A"), 4,4'-dihydroxy-diphenylmethane ("bisphenol F") and its isomers having hydroxy groups in different positions on the aromatic rings, 4,4'-dihydroxy-diphenylether, 4,4'-dihydroxy-diphenylsulfone ("bisphenol S"), hydroquinone and those hydroquinones which contain various substituents on their benzene ring, resorcinol, pyrocatecol, phloroglucinol, methyl-phloroglucinol, 1,1,3-tris-(4-hydroxyphenyl)propane, tris(4-hydroxyphenyl)methane, 2,2', 4,4'-tetrahydroxy-biphenyl, chlorinated or brominated bisphenols, such as 2,2-bis(4-hydroxy-3,5-dichlorophenyl)propane ("tetrachlorobisphenol A") and 2,2-bis(4-hydroxy-3,5-dibromophenyl)propane ("tetrabromobisphenol A"), as well as the polyglycidylethers of novolacs, these latter being obtained by means of the polycondensation, in particular acid-catalyzed polycondensation, of phenols with aldehydes, such as phenol-formaldehyde and orthocresol-formaldehyde novolaks.

Other polyepoxides, which can be used according to the present invention, comprise the polyglycidylesters of polycarboxylic acids of aliphatic, cycloaliphatic, aromatic or mixed character, such as adipic acid, linoleic acid dimer or trimer, hexahydrophthalic acid, methylhexahydrophthalic acid, 1,4-cyclohexanedioic acid, phthalic acid, isophthalic acid, as well as the polyglycidylesters of polycarboxylic acids which can be obtained by means of the reaction of one mole of a polyol containing "q" hydroxy groups with "q" moles of a cycloaliphatic or aromatic dicarboxylic acid or the corresponding anhydride or acid chloride.

Suitable polyepoxides for the compositions of the present invention, are also those which can be obtained by means of the N-alkylation of an aromatic amine, or N-alkylation and etherification of an aminophenol, with epichlorohydrin. Such a type of polyepoxides include N,N-diglycidyl-aniline, N,N,N',N'-tetraglycidyl-4,4'-diaminodiphenylmethane, N,N,N',N'-tetraglycidyl-4,4'-diaminodiphenylsulfone, N,N-diglycidyl-4-glycidoxy-aniline, and the mixtures of said compounds with the oligomers respectively formed in the synthesis reaction thereof with epichlorohydrin.

Furthermore, N-glycidylamides can be used, such as, e.g., N,N'-diglycidyloxamide, as well as several polyepoxides containing heterocyclic structures in their molecule, such as triglycidyl-isocyanurate, 1,2,4-triglycidyl-1,2,4-triazolinedione, polyglycidyl-1,3-bis(3-hydantoinyl)-2-hydroxypropane.

Suitable polyepoxides are also the poly(2-methylglycidyl)esters of the polycarboxylic acids mentioned above, as well as poly(2-alkyl-glycidyl)ethers of bisphenols and polyhydric phenols, such as the bis(2-methylglycidyl)ether of bisphenol A.

Further polyepoxides, which can be used according to the present invention, are the oligomeric diglycidylethers of bisphenols and mixtures thereof with the correspondent monomeric diglycidylethers of bisphenols hereinabove referred, which are obtained during the alkylation reaction of a bisphenol, with epichlorohydrin. As reported in the above references regarding the epoxy compounds, the degree of oligomerization of said oligomeric diglycidylethers is related to the epichlorohydrin to bisphenol molar ratios used in the alkylation reaction, which ratios are preferably comprised in the range from 2 (higher molecular weight oligomers) to 5 (monomeric and dimeric diglycidylether mixtures).

According to another widely used method for obtaining oligomeric diglycidylethers of bisphenols, the monomeric diglycidylether of a bisphenol is reacted with more bisphenol in a mutual molar ratio higher than 1. The average molecular weight of the product obtained depends from said molar ratio and it increases as the ratio approaches the value of 1.

Preferred oligomeric diglycidylethers are based on bisphenol A, particularly in admixture with one another and with bisphenol A diglycidylether. Such oligomers or mixtures thereof are represented by the following general formula:

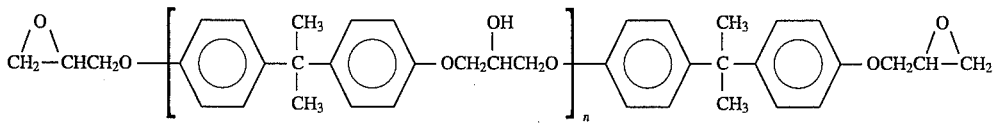

wherein the average degree of oligomerization "n" is a decimal number comprised within the range of from 0.2 to 30.

Further preferred oligomeric diglycidylethers are the diglycidylethers corresponding to the previous ones, which are obtained from bisphenol F.

Still further polyepoxides suitable for the present invention, are the polyglycidylethers of such aliphatic or cycloaliphatic polyols as 1,4-butanediol, 1,6-hexanediol, neopentylglycol, 1,4-dimethylol-cyclohexane, hydrogenated bisphenol A, polypropylene glycol, glycerol, 1,1,1-trimethylolpropane, pentaerythritol, and castor oil.

Other polyepoxides which can be used are those attainable by polyepoxidation, e.g. with peracids, of compounds containing 2, or more, olefinic double bonds, such as butadiene, 1,5-cyclooctadiene, 1,5,9-cyclododecatriene, bicyclopentadiene, 3-vinylcyclohexene, divinylbenzene, 4,4'-diallyldiphenylether, 2,2-bis(4-allylcyclohexyl)propane, polyunsaturated olefins containing 2, or more, cyclohexene rings or cyclopentene tings linked to one another by bridges comprising one or more atoms, such as bis(2-cyclopentenyl)ether, 2-(3-cyctohexenyl)-5,5-spiro-(cyclohex-3-ene)metadioxane, 3-cyclohexenylmethyl-3-cyclohexanoate, bis(3-cyclohexenylmethyl)adipate, esters of polyols with unsaturated carboxylic acids, such as vegetable oils, polymers and copolymers containing double bonds of olefinic character, such as polybutadiene, polyisoprene and their copolymers with other vinyl-monomers, such as styrene, as well as unsaturated polyesters. Finally, also comprised in the scope of the present invention are the polyepoxides consisting of polymers deriving from monomers containing epoxide groups, such as glycidyl acrylate, glycidyl methacrylate, allyl-glycidyl ether, and copolymers of said monomers with other vinyl-monomers, such as styrene, α-methylstyrene, vinyl acetate, alkyl acrylates and methacrylates.

According to the present invention, also mixtures of monoepoxides with polyepoxides of the type mentioned up to here, can be used as component (B). Said monoepoxides include, for instance, the glycidylethers of such alcohols as butanol, heptanol, octanol, 2-ethylhexanol, allyl alcohol, as well as the known glycidyl ethers of such phenols as phenol, paracresol, para-tertbutylphenol, and nonylphenol.

In the compositions of the present invention, said monoepoxides are preferably used in admixture with a major weight amount of polyepoxide. In particular, monoepoxides are preferably used in amounts of from 0 to 30% by weight, with respect to the total weight of the mono- and polyepoxide mixture.

For the preparation of the crosslinkable liquid compositions of the present invention, component (A) consisting of a polyisocyanate or a mixture of polyisocyanates and component (B) consisting of a polyepoxide alone or mixed with other polyepoxides or, optionally, monoepoxides, according to what is specified before, are combined in such quantities that the molar ratio between the isocyanate groups (—NCO) and the epoxy groups present in (A) and (B) respectively, is between 99/1 and 50/50, and preferably between 95/5 and 55/45.

The polymerization catalyst (C) is contained in the compositions of the present invention in a quantity of between 0.05 and 5, preferably between 0.1 and 1, parts by weight for 100 parts of (A) plus (B).

In addition to the above components (A), (B) and (C), the compositions of the present invention may additionally contain additives and auxiliaries, as well as their combinations, whose use is well known to experts in the field of plastic materials and thermosetting resins. These products are generally added to obtain polymeric materials having excellent characteristics for different specific applications, such as, for example, to improve the processability, increase the hardness, provide flame retarding properties, improve the mechanical properties, or simply reduce the cost of the material itself.

Among the additives of the known art which can be advantageously used for the purposes of the present invention, either alone or combined with each other, are mineral filler such as kaolin, talc, mica, calcium carbonate, dolomite, alumina, quartz or glass powder, titanium dioxide, various oxides, sulphides and chromates of heavy metals, carbon black, short or ground glass fibres, carbon fibres, asbestos fibres and other inorganic fibres; lubricating powders, such as graphite powder and molybdenum sulphide powder; flame retardants both inorganic such as antimonium trioxide, metallic borates and phosphates, and organic such as various polyhalogenated compounds, organic phosphates and phosphonates.

Other additives and auxiliary agents which can be used either alone or together with the above, comprise antioxidants, dyes, diluents, releasing agents, thixotropic agents, blowing agents, as well as antifoam agents, propellants, suspending agents, emulsifying agents and others whose use is known in the art.

In the particular case that, as specified also hereafter, the compositions of the present invention are used for the fabrication of finished or semi-finished articles in reinforced composite materials, they can contain strong fibres, continuous and/or cut into various lengths, such as glass fibres, carbon fibres, boron fibres, silicon carbide fibres, ceramic fibres, metal fibres, aramidic fibres or other known fibres and their combinations, arranged in different ways in ribbons, bands, strips, fabrics, unwoven fabrics, mats and the like, possibly combined with other structures or metal or non-metal inserts. These strong fibres are conveniently added in a quantity of from 0 to 70% by weight with respect to the total weight of the composition.

In general, the crosslinkable liquid compositions of the present invention are liquid at a temperature of 60° C., and preferably at 20° C., and can be rapidly convened into a solid polymeric material by a polymerization process under suitable conditions, caused by catalyst (C). These compositions are also characterized by a prolonged pot-life, usually from 1 to several hours, at temperatures ranging from room temperature to 70° C., after which they are still fluid and processable for a further period of time ranging from several hours to a few days, depending on the composition, the type of catalyst and environmental conditions.

At the same time, these compositions are surprisingly susceptible to hardening in rapid times, varying from several tens of seconds to tens of minutes, at temperatures of 40° C. or slightly higher, when subjected to microwave radiation. In addition, they are capable of hardening in times typically varying from a few tens of seconds to a few minutes when they are exclusively thermally heated to temperatures of 100° C. or more. The necessary times for the gelation and subsequent hardening of the present compositions, within the ranges indicated above, diminish with an increase in the treatment temperature, microwave radiation power and quantity of catalyst (C).

As already specified, the crosslinkable liquid compositions of the present invention can be advantageously and preferably hardened using a procedure to which the present invention also relates, and which comprises:

(i) mixing components (A), (B) and (C) and any additives until a homogeneous mixture is obtained;

(ii) charging the mixture prepared in (i) into an apparatus for treatment with suitably powerful electromagnetic radiation having a frequency within the range of 0.5 GHz to 20 GHz (microwaves range);

(iii) subjecting the mixture introduced into the apparatus of point (ii) to microwave radiation for a period of more than 0.5 minutes at a temperature not lower than 40° C., preferably between 40° and 80° C.

Preferably, in step (iii) of this procedure, the mixture is subjected to radiation for a period of between 1 and 30 minutes.

Any of the various methods suitable for the purpose and known in the field of thermosetting resins can be used for the preparation of the crosslinkable liquid compositions, in step (i) of the procedure of the present invention. The selection of the most suitable mixing method can be made each time by a normal technician in the field on the basis of the type of technology selected for the fabrication of the finished or semi-finished article to be obtained, as well as the production times desired or at least compatible with the gel time and hardening time of the composition.

In a typical non-limiting example, step (i) can be conveniently carried out by mixing components (A), (B) and (C) and other possible additives and auxiliary agents, in the suitable quantities, in a container with the help of a mixing/homogenizing apparatus selected among the numerous one available on the market on both an industrial and laboratory scale.

In another example, components (A) and (C,) or (B) and (C), can be premixed in the convenient quantities and with one or more of the additives or auxiliary agents in order to prepare two premixed components, and by mixing these in one of the apparatus mentioned above, the preparation of the compositions of the present invention is completed before their use. With respect to this, the complete freedom offered by the catalyst (C) of the present invention in selecting the operating conditions for the preparation of these compositions, is particularly advantageous. In fact, the catalysts (C) having the structural formula (III), are rapidly and completely soluble both in component (A) and in component (B), as well as in mixtures of both. In addition, the excellent stability of each single component and of the mixtures (A)+(C) or (B)+(C), which are capable of maintaining their original rheological characteristics for very long periods, of up to several months, at temperatures of up to 70° C., as well as the prolonged using time (of several hours) of the whole compositions at the same temperatures, enable both the single components and their mixtures to be heated to reduce the viscosity and thus making all dosaging, mixing, degassing operations under vacuum and all other necessary manipulations faster and more efficient. The possibility of having a using time which can be extended over a very long period, together with the surprising hardening rapidity with microwaves of the compositions of the present invention satisfies the requisites of a wide variety of processing technologies and guarantees great versatility of the present procedure, especially in cases where considerable quantities of solid particle additives, such as those mentioned above, mineral fillers, fibres or pigments are introduced into the mixture.

According to another example for the embodiment of the present invention, step (i) of the preparation of the above crosslinkable liquid compositions can be carried out, following well-known methods, by the simultaneous mixing in continuous of components (A) and (B) and the catalyst (C). This means that these are forced to flow, in suitable quantitative ratios, be sent and mixed in extremely short times, throught a duct, cavity, nozzle or similar geometrically suitable element, to form the homogeneous liquid composition, which is then directly fed to the device through which it is injected, sucked, poured or spread. In a variation of this method, the compositions of the present invention can be prepared with the same equipment, but by premixing, in suitable containers connected to the feeding lines, the catalyst (C) with component (A) or (B) respectively, or premixing components (A) and (B). The various optional additives and auxiliary agents are preferably premixed and homogeneously dispersed with one or both of components (A) or (B) or with one of the mixtures (A)+(B), (A)+(C) or (B)+(C).

In step (ii) of the procedure of the present invention, the composition prepared in step (i) is transferred or passed, in continuous or batch, into a microwave device with suitable shape and characteristics selected on the basis of the transformation technology used and on the form and dimensions of the finished or semi-finished articles desired.

According to step (iii) of the present procedure, the crosslinkable compositions of the present invention are hardened by subjecting them to radiation using a source of electromagnetic energy with frequencies within the microwave range. For this purpose, any equipment comprising a device for the emission of the microwaves connected to another chamber or duct consisting of a resonant cavity or wave guide, can be used. Numerous examples of these devices, which do not limit the present invention, are disclosed by J. Jow in the publication "Review of Scientific Instruments", vol. 60, n.1, page 96, (1989), whose content should be considered as forming an integral part of the present invention as reference.

A preferred apparatus for step (iii) of the present procedure comprises a single-mode resonant cavity. The present invention is not limited however to this apparatus, and can be satisfactorily embodied with other devices for microwave treatment.

The application of electromagnetic radiation in step (iii) of the present procedure can be either continuous or pulsed. In the former case the hardening times are shorter, but it becomes more difficult to control the temperature profile during polymerization, with the possible creation of local over-heating. In some cases it may be convenient to use electromagnetic radiation with modulated power.

In the procedure of the present invention, step (iii) can be conveniently carried out by applying pulsed radiation. This can be easily achieved by using a suitable oscillator inserted in the microwave circuit before the resonant cavity. The use of pulsed electromagnetic radiation enables excellent temperature control and, when required, allows the hardening procedure of the compositions to be carded out isothermally.

The hardening procedure with microwaves of the compositions of the present invention can be conveniently carded out using any of the methods and equipment of the known art suitable for the purpose. A wide variety of microwave generators is available on the market on both an industrial and laboratory scale, which can operate at a fixed frequency (typically 915 MHz and 2.45 GHz), or at varying frequencies within a wide range, typically between 0.5 and 20 GHz. These generators provide operating power varying from several tens of Watts up to 10 kW and more. Also the oscillators used for obtaining pulsed electromagnetic radiation are well known to experts in microwave technology. Examples of schematic representations of equipment for microwave treatment on a laboratory scale, suitable for the embodiment of the procedure of the present invention, are provided by J. Jow et al. in the publication "SAMPE Quarterly", January 1989, page 46, the contents of which is integrally comprised in the present application as reference.

In the procedure of the present invention, the selection of microwave radiation power, although of great practical importance, is not critical and can be easily made by a normal expert in the art on the basis of the technologies used, the dimensions of the articles formed, the characteristics of the crosslinkable composition, etc.

According to a preferred embodiment, the hardening procedure of the present invention is carried out by putting the crosslinkable liquid composition, typically shaped or cast into a suitably shaped mould, into the resonant cavity connected to the microwave generator and possible oscillator. The composition is then irradiated continuously or, preferably, by pulsed radiations, until the desired hardening degree is reached or until the end of the polymerization reactions. The best period and intensity of radiation are experimentally programmed for each single application of the procedure according to normal optimization methods available to experts in the field. The heating control of the mixture is generally obtained with a suitable temperature detector probe. At the end of the treatment, the hardened composition is removed from the cavity and, possibly, controlled.

According to a variation of the procedure of the present invention, steps (i), (ii) and (iii) previously described can also be carried out in succession in a single container or duct suitably shaped and prepared.

In a particular form of embodiment of the present invention, the procedure for hardening the crosslinkable liquid compositions described above comprises, during step (iii), in addition to the microwave radiation, and preferably, at the same time as or following this, also the application of thermal heating by exposure of these compositions to a source of heat. This additional thermal treatment is preferably carried out at temperatures ranging from 50° to 100° C. and for a period of from 1 to 30 minutes.

According to a preferred embodiment of the present invention, the solid polymeric material resulting from step (iii) rapidly hardened under the action of microwaves alone or of these combined with possible thermal treatment, is usually subjected to subsequent post-polymerization treatment (post-curing) at a higher temperature to complete the polymerization reactions.

This post-curing treatment of the already hardened composition can be carried out maintaining this at a temperature within the range of 80° to 250° C. and, preferably, between 120° and 220° C., for a period of 0.5 to 24 hours, preferably from 1 to 12 hours. In accordance with the present invention, also the post-curing treatment can be advantageously carried out by microwave radiation or by the combined action of microwaves and thermal treatment, using equipment and procedure basically similar to those previously described for the hardening step. The post-curing treatment does not necessarily require the removal of the formed article from the resonant cavity, but can be conveniently carried out in this by simply continuing the radiation and/or heating beyond the hardening step, under conditions which become progressively more and more intense.

The scope of the present invention does however comprise the possible post-curing treatment carried out by heating with only traditional thermal sources such as electric resistances, air or other hot gas heating, infrared sources, etc.

When the compositions of the present invention are subjected to hardening via thermal treatment alone, in this case, after step (i) of the procedure carried out as previously described, these are subjected to a hardening cycle in an oven or other thermal heating device, using one of the methods generally known by the expert in the art.

The crosslinkable liquid compositions of the present invention, with adequate hardening and post-curing treatment using one of the methods mentioned above, preferably carried out with microwaves, enable the production of formed, finished or semifinished articles, consisting of a polymeric material having a softening temperature of between 150° and 350° C., and preferably higher than 250° C., a considerable hardness, high elastic modulus value, good dielectric strength, good resistance to solvents and excellent resistance to hydrolysis and aggressive chemical products. Other characteristics of this polymeric material, also without additives, auxiliary agents or fibres, are the limited flammability and self-extinguishing properties, as well as the high tacking property to many substrates such as metals, glass materials and ceramics.

According to what is said hereinabove, the liquid reactive compositions of the present invention are particularly suitable, regardless of whether they are associated, or not, with various additives, reinforcing fibers or auxiliary agents, for rapid manufacturing of finished or semi-finished articles or devices, for heavy-duty thermal, mechanical, electrical and/or chemical applications.

In this regard, for example, a portion of the crosslinkable, liquid composition of the present invention, appropriately warmed to a temperature sufficient to impart the required fluidity, can be:

a) cast, injected, or sucked into open or closed molds to fabricate a variety of articles such as electrical insulators, connectors, switches, relays, etc.;

b) fed through pipes or hoses to a container for vacuum, pressure or combined vacuum/pressure embedding, encapsulation, or filling of inner cavities, of electrical/electronic devices, such as transformers, capacitors, resistors, etc.;

c) simply poured into a container where parts of electrical or mechanical devices, such as rotors or stators of electrical motors, turbines, etc., are timely dipped in for making insulating coatings, dust- and oil-protective coatings, etc.

Once the resin filling, with the related optional degassing, of the mold, container or cavities (or the resin spreading onto the surfaces to be treated) have been accomplished, the crosslinkable liquid composition is smoothly and rapidly polymerized by suitable microwave irradiation. The curing process may then be led to completion by continuing the irradiation, or by submitting the article or the device to a separate post-curing treatment, according to what is said hereinabove.

The compositions of the present invention are also particularly suitable for fast, continuous manufacture of such finished or semi-finished parts as beams, bars, draw pieces, plates, and pipes made in structural composite material by the known pultrusion or pulforming technologies, preferably on-line modified for use of the microwave curing process. To this purpose, the crosslinkable composition, at a temperature lower than 70° C., but still high enough as to assure the required fluidity of the same, can be continuously co-extruded together with bundles, strands, tapes, braids, fabrics, non-woven fabrics, and the like, of reinforcing fibers made of glass, carbon, polyaramid (Kevlar®) ecc., as well as metal wires or strips, which are thus continuously impregnated and embedded into the liquid composition itself. The batchwise-prepared composition, appropriately prepared before the extrusion, may be stored in a suitable tank from which it is continuously pumped and delivered to the impregnation zone of the apparatus before the extrusion die.

According to the present invention, the overall mixture, including the liquid crosslinkable composition, the fibrous structures and the other optional components, may be rapidly caused to harden by continuously passing through (e.g. carded by a conveyor belt) a suitable microwave irradiation apparatus, such as a tunnel or tubular microwave furnace, a microwave guide or the like, or a corresponding combined or co-assembled microwave/thermal device, placed just after the same die.

Analogously to what has been generally said above about the microwave processing, also when the present process and crosslinkable compositions are used in pultrusion or pulforming transformations, it is preferable to use a post-curing cycle after the curing step. Said post-curing cycle can be performed by submitting the hardened parts to microwave, thermal or combined heating, though the appliance, total or in part, of microwaves is preferred, since it may ensure a better quality of the finished articles. In this case too, such a post-curing may be suitably performed continuously at the end of the same production line as above.

The compositions and the process according to the present invention are furthermore suitable for being used for rapidly coating the surfaces of various articles and devices for protecting or insulating purposes, as well as for rapidly glueing or repairing parts of articles, or also for rapidly sealing junctures or crevices between different parts of articles. Accordingly, the liquid crosslinkable compositions can be prepared aliquot-by-aliquot, or also by continuous, on-line mixing of the components thereof, and then be spread onto surfaces, or injected into junctures or crevices concerned by the sealing treatment, and caused to rapidly harden by microwave irradiation. As an important advantage offered by the present finding when used as above, and however not limited thereto, the microwave irradiation can cause the hardening of the compositions with no need of the overall, bulk heating of the articles involved in the coating, glueing or repairing operations, thus clearly sparing time and energy, and possibly treating articles comprising parts which are heat-sensitive, but inert to microwave heating.

When used as a coating, the crosslinkable compositions of the present invention can comprise, in addition, known extenders or solvents, which may reduce the viscosity and promote the liability thereof, and can subsequently be removed by volatilization at suitable temperatures before the curing stage.

The present invention is illustrated in detail by the following examples, which, in turn, are supplied for merely indicative, non-limitative purposes within the scope of the same invention.

EXAMPLES

In the following examples all of the microwave polymerization experiments are performed utilizing an equipment purchased from Wavemat, Inc. in Plymouth Mich., which is characterised by a 7 inch diameter single-mode tuneable cavity. The equipment consists essentially of a variable power generator of electromagnetic radiation, which operates at a frequency of 2.45 GHz, with a maximum output power of 40 watts, and of a programmable temperature controller. Using this setup, it is possible to perform both constant power curing of the compositions of the present invention, monitoring the temperature as a function of time, and isothermal curing by pulsing the microwave power through the use of a controlled loop feedback sequence. When needed, the temperature is monitored using a Luxtron 755 fluoroptic system. The crosslinkable mixtures to be irradiated during the curing cycle are usually placed in containers made of Teflon in order to minimize the energy which is absorbed by the container and have a more precise output from the control and recording units. At the beginning of the polymerization, the temperature probe is immersed in the bulk of the liquid crosslinkable composition, where it becomes then embedded after curing has been completed. The sample temperature is thus accurately measured as a function of time.

In the following examples, viscosity of the liquid crosslinkable compositions is measured by using a Brookfield viscometer (Brookfield viscosity). The glass transition temperature of the compositions ($T_g$) after curing is obtained from the measurement of the dielectric constant and loss factor as a function of temperature, by dielectric thermal analysis on a DETA, Polymer Laboratory, analyzer. According to these measurements, the $T_g$ is defined as the temperature at which a peak occurs in the loss factor/sample temperature diagram If this temperature cannot be accurately determined, a working definition of the $T_g$ is used as the temperature at which the beginning of a quick increase of the loss factor is observed.

EXAMPLE 1

0.42 g of benzyltrimethylammonium hydroxide 40% by weight in methanol are dissolved in 17.00 g of 3-dimethylaminopropan-1-ol, in a round-bottomed, three-necked glass flask of 100 ml capacity, fitted with reflux condenser, thermometer and dropping funnel. To this solution, cooled to 0° C. in an ice/water bath, 8.75 g of freshly-distilled acrylonitrile are slowly added dropwise under magnetic stirring over a 15–20 minute period. During the addition period, the temperature is maintained at 20°–25° C. still by cooling in the ice/water bath. The mixture is still maintained 1 hour at room temperature under stirring, and then heated and maintained at 70° C. for 2 hours. After cooling to room temperature, 44.20 g of 1-iododecane are added dropwise with stirring. The resulting mixture is heated again to 70 ° C. and then kept at this temperature for 12 hours, during which time a gradual viscosity increase is observed.

Finally, after cooling to room temperature, an amber-colored liquid of honey-like consistency is obtained, which is indicated as Catalyst A A liquid crosslinkable composition is prepared, containing:

104.40 g of a crude methylendiphenyldiisocyanate (MDI), liquid at room temperature, having an isocyanate equivalent weight of 144.8 and a Brookfield viscosity of 48 cPs at 25° C.;

44.55 g of an epoxy resin consisting of the diglycidylether of bisphenol A, having an epoxy equivalent weight of 182.4 and a Brookfield viscosity of 8440 cPs at 25° C.;

1.05 g of the Catalyst A prepared as described above.

The composition is mixed until a homogeneous mixture is obtained, which has a Brookfield viscosity of 120 cPs at 25° C.

Two portions of 50 g each of the composition are poured into two glass vials. After sealing, one vial is left at the room temperature of 27° C., and the other one is placed in a thermostatic chamber at 50° C., for the pot-life determination at such two temperatures. Both at 27° and 50° C., a pot-life of 1 hour can be considered based on the detected increase of viscosity, although gelation is not reached in both cases. After this time, indeed, the composition remains liquid and still moldable, though highly-viscous, for at least further 5 hours.

Rapid thermal hardening of the as prepared composition can be achieved at 110° and at 130° C. in only 10 and 3.5 minutes, respectively.

A freshly prepared 3 g portion of the said liquid crosslinkable composition is used for a microwave curing experiment, with the above described procedure and equipment. Accordingly, the sample is irradiated by applying 9 watts of power for a total time of 15 minutes. A maximum temperature of 59 ° C. is reached after 7 minutes from the beginning of irradiation. At the end of the 15 minute period, a solidified sample is obtained characterized by a glass transition temperature of 50 ° C., as determined by dielectric measurements, using a heating rate of 2° C./rain and a frequency of 1 kHz. Meanwhile, for comparative purposes, another sample having the same above composition, is placed in a conventional hot-air oven and treated according to a similar temperature versus time profile, yielding at the end a still liquid material.

The glassy material resulting from the 15 minute period of microwave irradiation is submitted to a conventional thermal post-curing treatment, performed by a heating ramp up to 300° C. at 2° C./rain. The so post-cured material exhibits a glass transition temperature of about 275° C., as measured by DETA.

EXAMPLE 2

The same liquid crosslinkable composition as previously prepared in Example 1, is used for a microwave curing treatment under isothermal conditions. Accordingly, a sample of 3.4 g of the said freshly prepared composition is placed in the same above described single-mode microwave cavity, and irradiated for 15 minutes in such a way as to maintain a constant sample temperature of about 66° C. This is accomplished by turning the power generator on and off alternatively, thus obtaining a pulsed radiation. During the 15 minute irradiation period, the temperature varies from 65.9° to 70.6° C., indicating that reasonable isothermal control during the polymerization reaction is achieved.

At the end of the experiment, a sample of solidified material is removed from the microwave cavity, having a glass transition temperature of 60° C., as determined by dielectric measurements. The specimen is further treated with a conventional thermal post-curing in oven for one hour at 160° C. and one more hour at 180° C. The so obtained material shows a glass transition temperature of about 280° C., as determined by DETA.

For the sake of comparison, 20 g of the above fresh composition are maintained in a conventional thermostatic chamber at the same average temperature of 66° C. as used for the sample previously microwave cured. By contrast to the previous result, after 40 minutes the sample results to be simply gelled, but still soft, and remains as such for at least further 3 hours.

EXAMPLE 3

A liquid catalyst is prepared according to the same procedure adopted in Example 1. Thus, 17.67 g of N-(2-hydroxyethyl)morpholine, 0.094 g of benzyltrimethylammonium hydroxide 40% by weight in methanol, 7.15 g of acrylonitrile, and 24.80 g of 1-iodobutane are made to react. At the end, a catalyst is obtained, named Catalyst B, which appears to be a brown, highly-viscous liquid, at room temperature.

A liquid crosslinkable composition according to the present invention is prepared by mixing at room temperature:

70.20 g of the same "crude MDI" used in Example 1;

29.80 g of the same epoxy resin used in Example 1;

0.485 g of the Catalyst B prepared as described above.

Based on the detected increase of viscosity, the composition results to have a pot-life of at least 4 hours both at 27° and 50° C., as determined on 50 g portions as described in Example 1 above; in any case gelation takes place not before 36 hours.

A 3.1 g sample of the as prepared fresh composition is subjected to microwave curing according to the same procedure and with the same equipment as described in example 1, above, by applying 15 watts of power for a total time of 15 minutes. The maximum temperature measured during this period is 84° C., which is reached after 7 minutes. At the end of the experiment, a solid homogeneous sample is obtained, having a glass transition temperature of 75° C. Further conventional thermal post-curing of 1 hour at 190° C. yields a material with a $T_g$ of 255° C.

Comparatively, in a conventional thermal curing experiment carried out by heating a similar sample at 65°, at least 2 hours are required for even the gel point to occur.

EXAMPLE 4

An isocyanic prepolymer, liquid at room temperature, is prepared by reacting 200 g of the same "crude MDI" used in Example 1, with 50.0 g of a polyesterdiol from adipic acid, ethylene glycol and 1,4-butanediol (with a molar ratio of the two diols 1/1 each other), having an average molecular weight of 2089. The reaction is carried out by mixing the reagents for 2 hours at 80° C. in a 500 ml glass flask, equipped with mechanical stirrer, in the presence of 0.075 g of benzoyl chloride.

A liquid catalyst is then prepared, according to the same synthetic method as described in Example 1. To this aim, 14.58 g of 3-dimethylamino-2-propanol, 0.066 g of tetramethylammonium hydroxide pentahydrate, 7.50 g of acrylonitrile, and 37.90 g of 1-iododecane are reacted. At the end, a catalyst is obtained, named Catalyst C, which appears to be a yellowish, highly-viscous liquid, at room temperature.

A liquid crosslinkable composition according to the present invention is prepared by mixing at room temperature:

70.00 g of the above prepared isocyanic prepolymer;
29.75 g of the same epoxy resin as used in Example 1;
0.25 g of the above prepared Catalyst C.

Such a composition resulted in having a pot-life of at least 1 hour at 50° C., as measured on samples of 30 g, according to what described in example 1, above.

Said liquid crosslinkable composition is subjected to a microwave curing treatment under isothermal conditions, according to what described in example 2, above. To this aim, a sample of 15 g of the fleshly prepared composition is placed in the single-mode resonance cavity and irradiated for 15 minutes in such a way as to maintain a constant sample temperature of about 65 ° C. The maximum temperature range is from 64.5° to 66.3° C., indicating that an excellent isothermal control during the polymerization reaction is achieved.

At the end of the experiment, a specimen of solidified material is removed from the resonance cavity, having a glass transition temperature of 40° C., as determined by DETA. The specimen is further subjected to thermal post-curing, by heating thereof in a conventional oven, at a rate of 2° C./min up to 260° C. The so post-cured material has a glass transition temperature of about 245° C.

For the sake of comparison, an analogous sample of the above fresh composition is maintained in a conventional thermostatic chamber at the same average temperature of 65° C. as used for the sample previously microwave cured. 15 minutes after the sample is still liquid; further 15 minutes after it assumes a pasty appearance, and after additional 15 minutes, it results in having a rubbery consistency (gel).

EXAMPLE 5

A liquid catalyst is prepared substantially according to the same procedure adopted in Example 1. To this aim, 19.10 g of N-(2-hydroxyethyl)pyrrolidine, 0.104 g of benzyltrimethylammonium hydroxide 40% by weight in methanol, 8.80 g of acrylonitrile, and 32.03 g of 1-bromooctane are made to react. In this preparation, however, contrary to example 1, the quaternization stage with the alkyl bromide is accomplished in 6 hours at 70° C. followed by 12 hours at 85° C. At the end, a catalyst is obtained, named Catalyst D, which appears to be an amber-like, highly-viscous liquid, at room temperature.

A liquid crosslinkable composition according to the present invention is prepared by mixing at room temperature:

89.37 g of a "polymeric MDI", liquid at room temperature, having an isocyanate equivalent weight of 133.2 and a Brookfield viscosity of 72 cPs at 25° C.;

59.74 g of a polyglycidyl-novolac having an epoxy equivalent weight of 175.4, which is obtained from phenol and formaldehyde, followed by reaction with epichlorohydrin;

0.89 g of the above prepared Catalyst D.

Such a liquid crosslinkable composition is subjected to a microwave curing treatment under isothermal conditions, according to what described in example 2, above. To this aim, a sample of 30 g of said fleshly prepared composition is placed in a Teflon beaker of diameter 5 cm and depth 3 cm, and then transferred to the single-mode resonance cavity and microwave irradiated for 30 minutes in such a way as to maintain a constant sample temperature of about 70° C.

At the end of the experiment, a disk of diameter of 5 cm and thickness 1.5 cm of a hard, glassy material was removed from the teflon beaker. The disk is subjected to subsequent post-curing (1 h at 120° C., 1 h at 160° C., 1 h at 200° C. and 1 h at 240° C. successively), at the ent of which it results in having no deformation and exhibits a glass transition temperature in excess of 300° C., as determined by DETA.

For the sake of comparison, a second 30 g sample of the above fresh composition is maintained in a conventional thermostatic chamber at the same temperature of 70° C., for a period of 30 minutes, but, contrary to what previously obtained, it results still liquid after this period.

EXAMPLE 6

0.15 g of benzyltrimethylammonium hydroxide 40% by weight in methanol are dissolved in 26.49 g of N-(2-hydroxyethyl)morpholine, in a round-bottomed, three-necked glass flask of 100 ml capacity, fitted with reflux condenser, thermometer and dropping funnel. To this solution, cooled to 0° C. in an ice/water bath, 13.55 g of freshly distilled crotononitrile are slowly added dropwise under magnetic stirring over a 15–20 minute period. During the addition period, the temperature is maintained at 20°–25° C. still by cooling in the ice/water bath. The mixture is still maintained 1 hour at room temperature under stirring, and then heated and maintained at 70° C. for 6 hours. After cooling to room temperature, 40.00 g of 1-iodopentane are added dropwise with stirring. The resulting mixture is heated to 80 ° C. and then kept at this temperature for 14 hours, during which time a gradual viscosity increase is observed.

Finally, after cooling to room temperature, an amber-colored liquid of honey-like consistency is obtained, which is indicated as Catalyst E A liquid crosslinkable composition is prepared, containing:

104.40 g of the same crude MIDI as previously used in example 1;
44.82 g of an epoxy resin consisting of the diglycidylether of bisphenol F, having an epoxy equivalent weight of 167.5 and a Brookfield viscosity of 2485 cPs at 25° C.;
0.78 g of the Catalyst E prepared as described above.

The composition is mixed until a homogeneous mixture is obtained, which has a Brookfield viscosity of 96 cPs at 25° C.

Such a composition resulted in having a pot-life of about 2 hours at 60° C., as measured on samples of 30 g, according to what described in example 1, above. It resulted also to have a thermal hardening time at 110° and 130° C., of 10 and 4 minutes, respectively.

A freshly prepared 2.4 g sample of the said liquid crosslinkable composition is placed in a teflon container and transferred into the same microwave apparatus as previously described. The sample is irradiated by applying 9 watts of power for a total time of 15 minutes. For the first three minutes, a temperature increasing rate of about 8° C./min. is observed. Having reached a temperature of 50° C., the temperature suddenly increases 28° C. in 1 minute, thus indicating the occurrence of an exothermic polymerization reaction. A maximum temperature of 78° C. is reached.

At the end of the 15 minute period, a solidified glassy sample is obtained which is submitted to a post-curing by utilizing a combination of microwave and conventional thermal treatments. Accordingly, the sample is first post-cured for further 15 minutes at an average temperature of 145° C. by microwave irradiation, and subsequently is maintained at 200° C. for 1 hour by using conventional thermal heating. The glass transition temperature after the microwave post-curing resulted to be 180° C., and the final glass transition temperature after thermal treatment was 280° C.

EXAMPLE 7

A crosslinkable composition is prepared, which contains:

35.15 g of the same "polymeric MDI" used in Example 5 above;

14.60 g of the same epoxy resin used in Example 5 above;

0.25 g of Catalyst B prepared according to what described in Example 3; and 50.00 g of quartz powder, previously hot-dried at 200 ° C. for 2 hours.

All the components are mixed at room temperature. The quartz powder is pre-mixed with the pure isocyanate until an homogeneous mixture is obtained, to which the other components are then added and incorporated. The paste-like composition resulted in having a pot-life of about 5 hours at 30° C., as measured on samples of 30 g, according to what described in example 1, above.

70 g of the so obtained composition are warmed at 50 ° C. and vacuum degassed at this temperature for 1 hour at 100 torrs, and then for a further hour at 1 torr. A 3 g sample of this mixture is transferred to a Teflon container which is placed into the above described microwave cavity. The sample is irradiated by applying 34 watts of power for a total time of 30 minutes. It is necessary to use this level of power, due to the high quartz content of the sample. After a 7 minute irradiation, a maximum temperature of 105° C. is reached. At the end, a sample consisting of a hard material is obtained, which after post-curing for 2 hours at 220° C. shows a glass transition temperature of 315° C. (as determined by DETA).

EXAMPLE 8

A liquid catalyst is prepared by following a procedure substantially similar to that of Example 5. To this aim, 11.80 g of 2-dimethylaminoethanol, 0.31 g of benzyltrimethylammonium hydroxide 40% by weight in methanol, 8.88 g of crotononitrile, and 29.28 g of 1-bromodecane are made to react. At the end, a catalyst is obtained, named Catalyst F, which appears to be a brown, highly-viscous liquid.

A liquid crosslinkable composition according to the present invention is prepared by mixing at room temperature:

29.60 g of the same crude MDI as previously used in example 1;

119.40 g of the same epoxy resin used in Example 1;

1.00 g of the Catalyst F prepared as described above.

The composition resulted in having a pot-life of more than 4 hours at 27° C., as measured on samples of 30 g, according to the same method as described in example 1, above.

Such a liquid crosslinkable composition is subjected to a microwave curing treatment under isothermal conditions, according to what described in example 2, above. To this aim, a sample of 6 g of said fleshly prepared composition is placed in the Teflon beaker and then transferred to the single-mode resonance cavity and microwave irradiated for 25 minutes in such a way as to maintain a constant sample temperature of about 68° C.

At the end of the experiment, a hard, glassy material is removed from the teflon container. Subsequent post-curing by gradually heating the piece up to 300° C., at a rate of 5° C./min, produces a material with a glass transition temperature of about 280° C., as determined by DETA.

For the sake of comparison, an analogous sample of the above fresh composition is maintained in a conventional thermostatic chamber at the same temperature of 68° C., for a period of 25 minutes, but, contrary to what previously obtained, it results still liquid after this period and takes at least 1 hour to become a paste.

We claim:

1. A crosslinkable liquid composition based on organic isocyanate and epoxy compounds, polymerizable at temperatures of 40° C. or higher by exposure to non-ionizing electromagnetic radiation having a frequency in the microwave range, to obtain a solid material, said composition comprising:

(A) at least one organic polyisocyanate;

(B) at least one polyepoxide or mixture of a polyepoxide and a monoepoxide; and (C) from 0.05 to 5 parts by weight per 100 parts of the sum of (A) and (B), of a catalyst comprising at least one cyano compound containing a quaternary nitrogen atom and having formula (III)

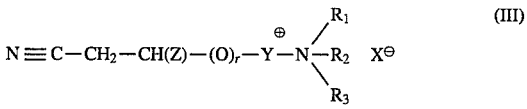

(III)

wherein

Z is hydrogen, a $C_{1-10}$ aliphatic radical, a $C_{3-10}$ cycloaliphatic radical, a $C_{3-10}$ heterocyclic radical, or a $C_{6-10}$ aromatic radical;

Y is a non-monovalent $C_{2-16}$ aliphatic organic radical, a $C_{5-16}$ cycloaliphatic radical, a $C_{5-16}$ heterocyclic radical, or a $C_{6-16}$ aromatic radical;

$R_1$ and $R_2$, which may be the same or different, are independently an aliphatic, cycloaliphatic, aromatic or heterocyclic radical, or $R_1$ and $R_2$ are linked together to form a heterocyclic, aliphatic or aromatic ring containing at least 5 ring atoms and containing a quaternary nitrogen atom, wherein $R_1$ and $R_2$ contain a total of 2–20 carbon atoms, or Y and $R_1$, or Y, $R_1$ and $R_2$, are linked together to form a heterocyclic, monocyclic, bicyclic, aliphatic or aromatic ring containing at least 5 ring atoms and containing a quaternary nitrogen atom;

$R_3$ is a $C_{1-20}$ aliphatic radical or a $C_{7-20}$ aryl-alkyl radical;

r is 0 or 1; and

X is a halide anion selected from the group consisting of chloride, bromide and iodide.

2. The liquid composition of claim 1, wherein $R_1$ and $R_2$, Y and $R_1$, or Y, $R_1$ and $R_2$ are linked together to form a ring and said ring contains 5–8 ring atoms.

3. The liquid composition of claim 1, wherein r is 1.

4. The liquid composition of claim 1, comprising 0.1–1.0 parts by weight of said catalyst per 100 parts of the sum of (A) and (B).

5. The liquid composition of claim 1, wherein said organic polyisocyanate has formula (XXVI)

Q(NCO)$_m$             (XXVI)

wherein m is a decimal number greater than 1; and

Q is a C$_{4-24}$ aliphatic, cycloaliphatic, aromatic or heterocyclic m-valent radical or a combination thereof.

6. The liquid composition of claim 5, wherein m is a decimal number in the range from 2 to 4.

7. The liquid composition of claim 5, wherein Q is a C$_{6-24}$ aromatic or cycloaliphatic radical.

8. The liquid composition of claim 1, wherein said polyisocyanate is liquid at 60° C.

9. The liquid composition of claim 1, wherein the average number of epoxy groups per molecule of said polyepoxide is a decimal number greater than 1.

10. The liquid composition of claim 9, wherein the average number of epoxy groups per molecule of said polyepoxide is between 1.8 and 4.0 inclusive.

11. The liquid composition of claim 1, wherein said polyepoxide is selected from the group consisting of glycidyl ethers of bisphenols and glycidyl ethers of novolacs.

12. The liquid composition of claim 1, wherein the molar ratio of isocyanate groups in said polyisocyanate to epoxy groups in said polyepoxide and monoepoxide is 99/1 to 50/50.

13. The liquid composition of claim 12, wherein said molar ratio is 95/5 to 55/45.

14. The liquid composition of claim 1, wherein said composition is liquid at 60° C.

15. The liquid composition of claim 14, when said composition is liquid at 30° C.

16. The liquid composition of claim 1, further comprising reinforcing fibers in an amount of 70% by weight or less, with respect to the weight of said liquid composition.

17. A process for polymerizing the liquid composition of claim 1 until a solid material is obtained, comprising the steps of:

(i) mixing said (A), (B) and (C) until a homogeneous mixture is obtained; and (ii) subjecting said mixture to microwave radiation having a frequency of 0.5–20 GHz for more than 0.5 minutes at a temperature not lower than 40° C.

18. The process of claim 17, wherein said mixture is subjected to microwave radiation at a temperature between 40°–80° C.

19. The process of claim 17, wherein said catalyst (C) is first mixed with said polyisocyanate (A) or said polyepoxide or mixture of polyepoxide and monoepoxide (B) and then mixed with the other of said (A) or (B).

20. The process of claim 17, wherein said mixture is subjected to microwave radiation for 1–30 minutes.

21. The process of claim 17, wherein said microwave radiation is pulsed radiation.

22. The process of claim 21, wherein said subjecting step is conducted at substantially constant temperature.

23. The process of claim 17, wherein said mixture is thermally heated during said subjecting step.

24. The process of claim 17, further comprising post-curing said solid material obtained from said subjecting step.

25. The process of claim 24, wherein said post-curing comprises heating said solid material at a temperature from 80°–250° C. for 0.5–24 hours.

26. The process of claim 25, wherein said post-curing comprises heating at a temperature between 120°–220° C. for 1–12 hours.

27. The process of claim 24, wherein said post-curing comprises further microwave irradiation of said solid material.

28. A crosslinked polymeric article obtained by the process of claim 17.

29. A crosslinked polymeric article obtained by the process of claim 24.

30. A crosslinkable liquid composition based on organic isocyanate and epoxy compounds, polymerizable at temperatures of 40° C. or higher by exposure to non-ionizing electromagnetic radiation having a frequency in the microwave range, to obtain a solid material, said composition comprising:

(A) at least one organic polyisocyanate;

(B) at least one polyepoxide or mixture of a polyepoxide and a monoepoxide; and (C) from 0.05 to 5 parts by weight per 100 parts of the sum of (A) and (B), of a catalyst comprising at least one cyano compound containing a quaternary nitrogen atom and having formula (III)

$$N\equiv C-CH_2-CH(Z)-(O)_r-Y-\overset{\oplus}{N}\begin{matrix}R_1\\ -R_2\\ R_3\end{matrix} \quad X^{\ominus} \qquad (III)$$

wherein

Z is hydrogen, a C$_{1-10}$ aliphatic radical, a C$_{3-10}$ cycloaliphatic radical, a C$_{3-10}$ heterocyclic radical, or a C$_{6-10}$ aromatic radical;

Y is a non-monovalent C$_{2-16}$ aliphatic organic radical, a C$_{5-16}$ cycloaliphatic radical, a C$_{5-16}$ heterocyclic radical, or a C$_{6-16}$ aromatic radical;

R$_1$ and R$_2$, which may be the same or different, are independently an aliphatic, cycloaliphatic, aromatic or heterocyclic radical, or R$_1$ and R$_2$ are linked together to form a heterocyclic, aliphatic or aromatic ring containing at least 5 ring atoms and containing a quaternary nitrogen atom, wherein R$_1$ and R$_2$ contain a total of 2–20 carbon atoms, or Y and R$_1$, or Y, R$_1$ and R$_2$, are linked together to form a heterocyclic, monocyclic, bicyclic, aliphatic or aromatic ring containing at least 5 ring atoms and containing a quaternary nitrogen atom;

R$_3$ is a C$_{1-20}$ aliphatic radical or a C$_{7-20}$ aryl-alkyl radical;

r is 0 or 1; and

X is a halide anion selected from the group consisting of chloride, bromide and iodide, wherein said catalyst is obtained by a process wherein an α,β-unsaturated nitrile of formula XXV

N≡C—CH=CH(Z)          XXV wherein Z is as defined above, is reacted with a tertiary hydroxyamino compound of formula XXIV

HO—Y—NR$_1$R$_2$          XXIV wherein Y, R$_1$ and R$_2$ are as defined above, or with a mixture of said hydroxyamino compound and with an alkyl monohalide of formula R$_3$X, wherein R$_3$ is as defined above and X is a chlorine, bromine or iodine atom;

according to the following steps:

I-a) said α, β-unsaturated nitrile is added to a liquid mixture containing said tertiary hydroxyamino compound, a strong base, and optionally a solvent or mixture of solvents, maintained at a temperature within the range of 0° to 80° C., wherein said strong base is present in an amount of 0.5–5 milliequivalents with respect to 100 g of the reaction mixture including said α,β-unsaturated nitrile;

I-b) the reaction mixture obtained in I-a is stirred for 0.5–6 hours at temperatures between 0° and 80° C.;

II-a) said alkyl monohalide is added to the mixture obtained in step I-b and stirred at a temperature between 0° and 40° C., stirring is continued for an additional 0.5–6 hours between 0° and 40° C.;

II-b) the mixture obtained in step II-a) is heated with stirring to a temperature between 50° and 120° C. and maintained at this temperature for 6–60 hours; and II-c) the optional solvent is removed by evaporation.

* * * * *

UNITED STATES PATENT AND TRADEMARK OFFICE
CERTIFICATE OF CORRECTION

PATENT NO. : 5,489,664

DATED : February 6, 1996

INVENTOR(S) : Fabrizio PARODI, et al.

It is certified that error appears in the above-identified patent and that said Letters Patent is hereby corrected as shown below:

Column 2, line 7, "Tipically" should read --Typically--.

Column 3, line 38, "quaternary 13-hydroxyalkylam-" should read --quaternary β-hydroxyalkylam- --;
line 49, "applications requiting" should read --applications requiring--.

Column 4, line 65, "plus 03)," should read --plus (B),--.

Column 5, line 18, "$R_1$ and $P_1$" should read --$R_1$ and $R_2$--.

Column 11, line 25, Delete "lo".

Column 12, line 14, "isocianic prepolymers" should read --isocyanic prepolymers--.

Column 13, line 65, "polyepoxydes or of polyepoxydes" should read --polyepoxides or of polyepoxides--.

Column 15, line 52, "cyclopentene tings" should read -cyclopentene rings--.

Column 17, line 12, "rapidly convened" should read --rapidly converted--.

UNITED STATES PATENT AND TRADEMARK OFFICE
CERTIFICATE OF CORRECTION

PATENT NO. : 5,489,664

DATED : February 6, 1996

INVENTOR(S) : Fabrizio PARODI, et al.

It is certified that error appears in the above-identified patent and that said Letters Patent is hereby corrected as shown below:

Column 18, line 1, "components (A) and (C,)" should read
--components (A) and (C),--.

Column 19, line 21, "to be carded out" should read
--to be carried out--.

line 24, "carded out" should read--carried out--.

Column 20, line 43, "semifinished articles" should read
--semi-finished articles--.

Column 21, line 31, "(Kevlar®) ecc" should read
--Kevlar®) etc--.
    line 42, "carded by a conveyor" should read
--carried by a conveyor--.

Column 22, line 56, Insert a period (.) After "diagram".

Column 23, line 51, "rate of 2°C/rain" should read
--rate of 2°C/min--.
    line 60, "300°C at 2°C/rain" should read
--300°C at 2°C/min--.

Column 26, line 51, "same crude MIDI" should read
--same crude MDI--.

UNITED STATES PATENT AND TRADEMARK OFFICE
CERTIFICATE OF CORRECTION

PATENT NO. : 5,489,664

DATED : February 6, 1996

INVENTOR(S) : Fabrizio PARODI, et al.

It is certified that error appears in the above-identified patent and that said Letters Patent is hereby corrected as shown below:

Column 27, line 31, "until an" should read --until a--.

Column 28, line 7, "said fleshly prepared" should read --said freshly prepared--.

Column 29, line 35, "claim 14, when" should read --claim 14, wherein--.

Signed and Sealed this

Nineteenth Day of May, 1998

Attest:

*Attesting Officer*

BRUCE LEHMAN

*Commissioner of Patents and Trademarks*